United States Patent [19]

Tomalia et al.

[11] Patent Number: 4,587,329

[45] Date of Patent: May 6, 1986

[54] DENSE STAR POLYMERS HAVING TWO DIMENSIONAL MOLECULAR DIAMETER

[75] Inventors: Donald A. Tomalia, Midland; James R. Dewald, Bay City, both of Mich.

[73] Assignee: The Dow Chemical Company, Midland, Mich.

[21] Appl. No.: 757,546

[22] Filed: Jul. 19, 1985

Related U.S. Application Data

[63] Continuation-in-part of Ser. No. 641,807, Aug. 17, 1984, which is a continuation-in-part of Ser. No. 456,226, Jan. 1, 1983, Pat. No. 4,507,466, which is a continuation-in-part of Ser. No. 565,686, Dec. 27, 1983.

[51] Int. Cl.$^4$ ............................................. C08G 69/00
[52] U.S. Cl. ................................... 528/363; 525/410; 525/416; 525/418; 525/451; 528/310; 528/332; 528/350; 528/373; 528/271; 528/374; 528/376; 528/397; 528/403; 528/405; 528/425
[58] Field of Search ............... 528/363, 332, 310, 350, 528/373, 374, 376, 397, 403, 405, 425; 525/410, 416, 418, 451

[56] References Cited

U.S. PATENT DOCUMENTS 4,507,466  3/1985  Tomalia et al. ..................... 528/363

OTHER PUBLICATIONS

Tomalia et al., Polymer Journal, vol. 17, No. 1, pp. 117–132 (1985).

*Primary Examiner*—Harold D. Anderson
*Attorney, Agent, or Firm*—M. S. Jenkins

[57] ABSTRACT

Dense star polymers having terminal group densities greater than conventional extended star polymers exhibit greater and more uniform reactivity than their corresponding conventional star polymers. For example, a third generation, hydroxy-terminated polyether dense star polymer can be prepared from pentaerythrityltetrabromide and 4-hydroxymethyl-2,6,7-trioxabicyclo[2.2.2]-octane which has a molecular volume less than 80 percent of the volume of a conventional extended star polymer made from similar materials. Such dense star polymers are useful as demulsifiers for oil/water emulsions, wet strength agents in the manufacture of paper, proton scavengers, calibration standards for electron microscopy, and agents for modifying viscosity in aqueous formulations such as paints.

17 Claims, No Drawings ium.

DENSE STAR POLYMERS HAVING TWO DIMENSIONAL MOLECULAR DIAMETER PER EXR

CROSS-REFERENCE TO RELATED APPLICATIONS

This application is a continuation-in-part of application Ser. No. 641,807, filed on Aug. 17, 1984, which is a continuation-in-part of application Ser. No. 456,226, filed on Jan. 1, 1983, now U.S. Pat. No. 4,507,466 and a continuation-in-part of application Ser. No. 565,686, filed on Dec. 27, 1983.

BACKGROUND OF THE INVENTION

This invention relates to a novel class of branched polymers containing dendritic branches having functional groups uniformly distributed on the periphery of such branches. This invention also relates to processes for preparing such polymers as well as applications therefore.

Organic polymers are generally classified in a structural sense as either linear or branched. In the case of linear polymers, the repeating units (often called mers) are divalent and are connected one to another in a linear sequence. In the case of branched polymers, at least some of the mers possess a valency greater than 2 such that the mers are connected in a nonlinear sequence. The term "branching" usually implies that the individual molecular units of the branches are discrete from the polymer backbone, yet have the same chemical constitution as the polymer backbone. Thus, regularly repeating side groups which are inherent in the monomer structure and/or are of different chemical constitution than the polymer backbone are not considered as branches, e.g., dependent methyl groups of linear polypropylene. To produce a branched polymer, it is necessary to employ an initiator, a monomer, or both that possess at least three moieties that function in the polymerization reaction. Such monomer or initiators are often called polyfunctional. The simplest branched polymers are the chain branched polymers wherein a linear backbone bears one or more essentially linear pendant groups. This simple form of branching, often called comb branching, may be regular wherein the branches are uniformly and regularly distributed on the polymer backbone or irregular wherein the branches are distributed in nonuniform or random fashion on the polymer backbone. See T. A. Orofino, Polymer, 2, 295–314 (1961). An example of regular comb branching is a comb branched polystyrene as described by T. Altores et al. in *J. Polymer Sci., Part A,* Vol. 3, 4131–4151 (1965) and an example of irregular comb branching is illustrated by graft copolymers as described by Sorenson et al. in "Preparative Methods of Polymer Chemistry", 2nd Ed., Interscience Publishers, 213–214 (1968).

Another type of branching is exemplified by crosslinked or network polymers wherein the polymer chains are connected via tetravalent compounds, e.g., polystyrene molecules bridged or cross-linked with divinylbenzene. In this type of branching, many of the individual branches are not linear in that each branch may itself contain groups pendant from a linear chain. More importantly in network branching, each polymer macromolecule (backbone) is cross-linked at two or more sites to two other polymer macromolecules. Also the chemical constitution of the cross-linkages may vary from that of the polymer macromolecules. In this so-called cross-linked or network branched polymer, the various branches or cross-linkages may be structurally similar (called regular cross-linked) or they may be structurally dissimilar (called irregularly cross-linked). An example of regular cross-linked polymers is a ladder-type poly(phenylsilsesquinone) as described by Sorenson et al., supra, at page 390. The foregoing and other types of branched polymers are described by H. G. Elias in *Macromolecules,* Vol. I, Plenum Press, New York (1977).

More recently, there have been developed polymers having so-called star structured branching wherein the individual branches radiate out from a nucleus and there are at least 3 branches per nucleus. Such star branched polymers are illustrated by polyquaternary compositions described in U.S. Pat. Nos. 4,036,808 and 4,102,827. Star branched polymers prepared from olefins and unsaturated acids are described in U.S. Pat. No. 4,141,847. The star branched polymers offer several advantages over polymers having other types of branching. For example, it is found that the star branched polymers may exhibit higher concentrations of functional groups thus making them more active for their intended purpose. In addition, such star branched polymers are often less sensitive to degradation by shearing which is a very useful property in formulations such as paints, in enhanced oil recovery and other viscosity applications. Additionally, the star branched polymers have relatively low intrinsic viscosities even at high molecular weight.

While the star branched polymers offer many of the aforementioned advantages over polymers having more conventional branching, it is highly desirable to provide polymers which exhibit even greater concentrations of functional groups per unit volume of the polymer macromolecule as well as a more uniform distribution of such functional groups in the exterior regions of the macromolecule. In addition, it is often desirable to provide polymers having macromolecular configurations that are more spheroidal and compact than are the star branched polymers.

SUMMARY OF THE INVENTION

In its broadest aspect, this invention is a dense star polymer having at least one branch (hereinafter called a core branch) emanating from a core, said branch having at least one terminal group provided that (1) the ratio of terminal groups to the core branches is more than one, preferably two or greater, (2) the density of terminal groups per unit volume in the polymer is at least 1.5 times that of an extended conventional star polymer having similar core and monomeric moieties and a comparable molecular weight and number of core branches, each of such branches of the extended conventional star polymer bearing only one terminal group, and (3) a molecular volume that is no more than about 80 percent of the molecular volume of said extended conventional star polymer as determined by dimensional studies using scaled Corey-Pauling molecular models. For purposes of this invention, the term "dense" as it modifies "star polymer" means that it has a smaller molecular volume than an extended conventional star polymer having the same molecular weight. The extended conventional star polymer which is used as the base for comparison with the dense star polymer is one that has the same molecular weight, same core and monomeric components and same number of core branches as the dense star polymer. By "extended" it is meant that the individual branches of the conventional star polymer are extended or stretched to their maximum length, e.g., as such branches exist when the star polymer is completely solvated in an ideal solvent for the star polymer. In addition while the number of terminal groups is greater for the dense star polymer molecule than in the conventional star polymer molecule, the chemical structure of the terminal groups is the same.

In a somewhat more limited and preferred aspect, this invention is a polymer having a novel ordered star branched structure (herein called starburst structure). Hereinafter this polymer having a starburst structure is called a dendrimer. Thus, a "dendrimer" is a polymer having a polyvalent core that is covalently bonded to at least two ordered dentritic (tree-like) branches which extend through at least two generations. As an illustration, an ordered second generation dendritic branch is depicted by the following configuration:

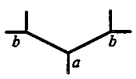

wherein "a" represents the first generation and "b" represents the second generation. An ordered, third generation dendritic branch is depicted by the following configuration:

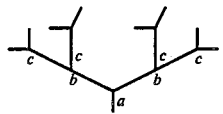

wherein "a" and "b" represent the first and second generation, respectively, and "c" represents the third generation. A primary characteristic of the ordered dendritic branch which distinguishes it from conventional branches of conventional polymers is the uniform or essentially symmetrical character of the branches as is shown in the foregoing illustrations. In addition, with each new generation, the number of terminal groups on the dendritic branch is an exact multiple of the number of terminal groups in the previous generation.

Another aspect of this invention is an excess reactant process for producing the dense star polymer comprising the steps of
(A) contacting
  (1) a core compound having at least one nucleophilic or one electrophilic moiety (hereinafter referred to in the alternative as N/E moieties) with
  (2) an excess of a first organic coreactant having (a) one moiety (hereinafter called a core reactive moiety) which is reactive with the N/E moieties of the core compound and (b) an N/E moiety which does not react with the N/E moiety of the core under conditions sufficient to form a core adduct wherein each N/E moiety of the core compound has reacted with the core reactive moiety of a different molecule of the first coreactant;
(B) contacting
  (1) the core adduct having at least twice the number of N/E moieties as the core compound with
  (2) an excess of a second organic coreactant having (a) one moiety (hereinafter called an adduct reactive moiety) which will react with the N/E moieties of the core adduct and (b) an N/E moiety which does not react with the N/E moiety of the core adduct under conditions sufficient to form a first generation adduct having a number of N/E moieties that are at least twice the number of N/E moieties in the core adduct; and
(C) contacting the first generation adduct with an excess of a third organic coreactant having one moiety that is reactive with the N/E moieties of the first generation adduct and an N/E moiety that does not react with the N/E moieties of the first generation adduct under conditions sufficient to form a second generation dendrimer. In the foregoing process, the first coreactant differs from the second coreactant, and the second coreactant differs from the third coreactant, but the first and third coreactants may be the same or different compounds. The third and higher generation dendrimers are formed by repeating steps (B) and (C) of the aforementioned process.

A further aspect of this invention is a partially protected reactant process for producing the dense star polyamine comprising the steps of
(A) contacting
  (1) a core compound have at least one N/E moiety
  (2) a first organic coreactant having a moiety which is reactive with the N/E moieties of the core oompound and (b) a blocking moiety (which does not react with the N/E moieties of the core) under conditions sufficient to form a blocked core adduct wherein each N/E moiety of the core compound has reacted with the reactive moiety of a different molecule of the first organic coreactant to form an adduct having blocked N/E moieties;
(B) removing the blocking moieties from the blocked core adduct to form a first generation adduct having N/E moieties;
(C) contacting
  (1) the first generation adduct which has at least twice the number of terminal N/E moieties as the core compound with
  (2) a second organic coreactant having a moiety which will react with the terminal N/E moieties of the first generation adduct and a blocking moiety (which does not react with the N/E moieties of the first generation adduct) under conditions sufficient to form a blocked second generation adduct having a number of blocked second generation adducts having a number of blocked N/E moieties that are at least twice the number of blocked N/E moieties in the blocked core adduct; and
(D) removing the blocking moieties from the blocked second generation adduct to form second generation adduct or dendrimer.

In the foregoing partially protected reactant process, the first and second organic coreactant used in the formation of the first and second generation dendrimers may be the same or different. The third and higher generation dendrimers are formed by repeating steps (C) and (D) of the afornentioned process, provided that such generations are not prevented by excessive dense surface packing of the terminal groups in such additional generations. By "dense surface packing", it is meant that the concentration of reactive moieties on the surface of the dense star polymer is so high that further reaction on a stoichiometric basis is prevented.

Other aspects of this invention are methods for using the dense star polymer in such applications as demulsifiers for oil/water emulsions, wet strength agents in the manufacture of paper, size selective membranes, high efficiency proton scavengers, and calibration standards for electron microscopy, agents for modifying viscosity in aqueous formulations such as paints, and the like. For example, in a demulsification method, an emulsion of oil and water is contacted with a demulsifying amount of the dense star polymer under conditions sufficient to cause phase separation.

The dense star polymers of the present invention exhibit the following properties which are unique or are superior to similar properties of conventional extended star branched polymers and other branched polymers having similar molecular weight and terminal groups:
(a) greater branch density;
(b) greater terminal group density;
(c) greater accessibility of terminal groups to chemically reactive species; and
(d) lower viscosity.

DETAILED DESCRIPTION OF ILLUSTRATIVE EMBODIMENTS

In the dense star polymers of the present invention, the core is covalently bonded to at least one core branch, preferably at least two, most preferably at least three, core branches with each core branch having a calculated length of at least 3 Angstrom units (Å), preferably at least 4 Å, most preferably at least 6 Å. These polymers preferably have an average of at least 2, more preferably at least 3 and most preferably at least 4 terminal groups per polymer molecule. Preferably, the core branches have a dendritic character, most preferably an ordered dendritic character as defined hereinafter.

The dense star polymers of this invention preferably have two-dimensional molecular diameters in the range from about 12 to about 2000 *Angstrom units (Å), more preferably from about* 25 Å to about 500 Å and most preferably from about 50 Å to about 250 Å. For the purposes of this invention, a two-dimensional molecular diameter is determined by the following electron microscopic method. First, the terminal groups of dendrimers are connected to anionic moieties (e.g., by hydrolysis of the terminal ester moieties of polyamidoamine dendrimer in half generation state). The anionic dendrimer molecules are then neutralized with stoichiometric amounts of alkali metal hydroxide. A dilute aqueous solution (e.g., about 0.5 weight percent of the neutralized dendrimer in water) of the dendrimer is placed on a beryllium grid (~1.5 millimeter diameter puddle) and allowed to evaporate. The dendrimer often exhibits dendritic-like crystalline growth during the evaporation process. The diameter of the dry dendrimer molecules in two-dimensional state are then measured by electron microscopy and found to correspond closely, e.g., within 15 percent, to the diameters predicted by scaled Corey-Pauling molecular models. Such measurements are readily made using a *JEM*-1200 *EX Electron Microscope* sold by JEOL Corporation using CTEM techniques on a beryllium grid coated with 50 Å carbon.

The dense star polymers of this invention preferably have three-dimensional molecular diameters in the range from about 6 to about 1000, more preferably from about 10 to about 250, most preferably from about 25 to about 125 Angstrom units. For the purposes of this invention, a three-dimensional molecular diameter is determined by calculating hydrodynamic diameters using the following Hester-Mitchell relationship, R. D. Hester et al., *J. Poly Sci.*, Vol. 18, p. 1727 (1980).

$$d = \left[\frac{240}{\pi N}\right]^{\frac{1}{3}} [M(\eta)]^{\frac{1}{3}}$$

wherein d is the hydrodynamic diameter in Angstrom units; N is $6.02 \times 10^{23}$; M is number average molecular weight of the dendrimer; $\pi$ is 3.14; and $\eta$ is intrinsic viscosity of the dense star polymer in deciliters per gram at 25° C.

In preferred dense star polymers, the terminal groups are functional groups that are sufficiently reactive to undergo addition or substitution reactions. Examples of such functional groups include amino, hydroxy, mercapto, carboxy, alkenyl, allyl, vinyl, amido, halo, urea, oxiranyl, aziridinyl, oxazolinyl, imidazolinyl, sulfonato, phosphonato, isocyanato and isothiocyanato. The dense star polymers differ from conventional star or star-branched polymers in that the dense star polymers have a greater concentration of terminal groups per unit of molecular volume than do conventional extended star polymers having an equivalent number of core branches and an equivalent core branch length. Thus, the density of terminal groups per unit volume in the dense star polymer is at least about 1.5 times the density of terminal groups in the conventional extended star polymer, preferably at least 5 times, more preferably at least 10 times, most preferably from about 15 to about 50 times. The ratio of terminal groups per core branch in the dense polymer is preferably at least 2, more preferably at least 3, most preferably from about 4 to about 1024. Preferably, for a given polymer molecular weight, the molecular volume of the dense star polymer is less than 70 volume percent, more preferably from about 16 to about 60, most preferably from about 7 to about 50 volume percent of the molecular volume of the conventional extended star polymer.

In the preferred polyether dense star polymers, the density of terminal functional moieties, usually hydroxy, in the polymer is readily expressed as the molar ratio of terminal functional moieties to the total ether moieties. In such polymers this molar ratio of terminal groups to ether groups is preferably from about 0.3:1 to about 4:1, more preferably from about 0.7:1 to about 3:1, most preferably from about 1:1 to about 2:1.

The preferred dendrimers of the present invention are characterized as having a polyvalent core that is covalently bonded to at least two ordered dendritic branches which extend through at least two generations. Such ordered branching can be illustrated by the following sequence wherein G indicates the number of generations:

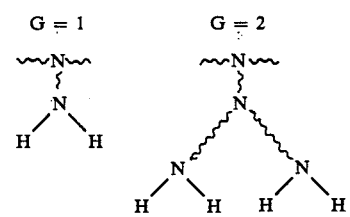

G = 3

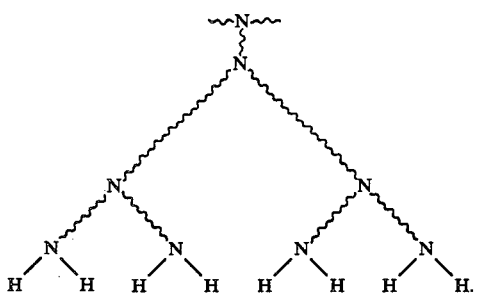

Mathematically, the relationship between the number of terminal groups on a dentritic branch and the number of generations of the branch can be represented as follows:

$$\text{\# of terminal groups per dendritic branch} = \frac{N_r^G}{2}$$

wherein G is the number of generations and $N_r$ is the repeating unit multiplicity which is at least 2 as in the case of amines. The total number of terminal groups in the dendrimer is determined by the following:

$$\text{\# of terminal groups per dendrimer} = \frac{N_c N_r^G}{2}$$

wherein G and $N_r$ are as defined before and $N_c$ represents the valency (often called core functionality) of the core compound. Accordingly, the dendrimers of the present invention can be represented in its component parts as follows:

$$\left[ (\text{Core}) \left[ (\text{Repeat Unit})_{\frac{N_r^G-1}{N_r-1}} \left( \begin{array}{c} \text{Terminal} \\ \text{Moiety} \end{array} \right)_{\frac{N_r^G}{2}} \right] \right] N_c$$

wherein the Core, Terminal Moiety, G and $N_c$ are as defined before and the Repeat Unit has a valency or functionality of $N_r+1$ wherein $N_r$ is as defined before.

A copolymer dendrimer which is preferred for the purposes of this invention is a unique compound constructed of polyfunctional monomer units in a highly branched (dendritic) array. The dendrimer molecule is prepared from a polyfunctional initiator unit (core compound), polyfunctional repeating units and terminal units which may be the same or different from the repeating units. The core compound is represented by the formula $①(Z^c)_{Nc}$ wherein $①$ represents the core, $Z$ represents the functional groups bonded to $①$ and Nc represents the core functionality preferably 2 or more, most preferably 3 or more. Thus, the dendrimer molecule comprises a polyfunctional core, $①$, bonded to a number (Nc) of functional groups, $Z^c$, each of which is connected to the monofunctional tail of a repeating unit, $X^1Y^1(Z^1)_{N1}$, of the first generation and each of the Z groups of the repeating unit of one generation is bonded to a monofunctional tail of a repeating unit of the next generation until the terminal generation is reached. In the dendrimer molecule, the repeating units are the same within a single generation, but may differ from generation to generation. In the repeating unit, $X^1Y^1(Z^1)_{N1}$, $X^1$ represents the monofunctional tail of the first generation repeating unit, $Y^1$ represents the moiety constituting the first generation, $Z^1$ represents the functional group of the polyfunctional head of the repeating unit of the first generation and may be the same as or different from the functional groups of the core compound, $①(Z)_{Nc}$, or other generations; and $N^1$ is a number of 2 or more, most preferably 2, 3 or 4, which represents the multiplicity of the polyfunctional head of the repeating unit in the first generation. Generically, the repeating unit is represented by the formula $X^iY^i(Z^i)_{Ni}$ wherein "i" represents the particular generation from the first to the t-1 generation. Thus, in the preferred dendrimer molecule, each $Z^1$ of the first generation repeating unit is connected to an $X^2$ of a repeating unit of the second generation and so on through the generations such that each $Z^i$ group for a repeating unit $X^iY^i(Z^i)_{Ni}$ in generation number "i" is connected to the tail ($X^{i+1}$) of the repeating unit of the generation number "i+1". The final or terminal of a preferred dendrimer molecule comprises terminal units, $X^tY^t(Z^t)_{Nt}$ wherein t represents terminal generation and $X^t$, $Y^t$, $Z^t$ and $N^t$ may be the same as or different from $X^i$, $Y^i$, $Z^i$ and $N^i$ except that there is no succeeding generation connected to the $Z^t$ groups and $N^t$ may be less than two, e.g., zero or one. Therefore the preferred dendrimer has a molecular formula represented by

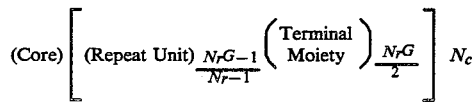

wherein the symbols are as previously defined. The $\pi$ function is the product of all the values between its defined limits. Thus $$\prod_{n=1}^{i-1} N^n = (N^1)(N^2)(N^3)(N^{i-2})(N^{i-1})$$

which is the number of repeat units, $X^iY^i(Z^i)_{Ni}$, comprising the ith generation of one dendritic branch. In copolymer dendrimers, the repeat unit for one generation differs from the repeat unit in at least one other generation. The preferred dendrimers are very symmetrical as illustrated in structural formulas described hereinafter. Preferred dendrimers may be converted to functionalized dendrimers by contact with another reagent. For example, conversion of hydroxyl in the terminal generation to ester by reaction with an acid chloride gives an ester terminally functionalized dendrimer. This functionalization need not be carried out to the theoretical maximum as defined by the number of available functional groups and, thus, a functionalized dendrimer may not have high symmetry or a precisely defined molecular formula as is the case with the present dendrimer.

An illustration of a functionally active dendrimer of a ternary or trivalent core which has three ordered, second generation dendritic branches is depicted by the following configuration;

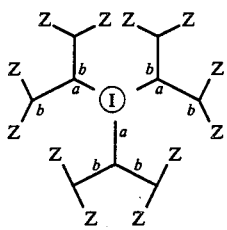

wherein Ⓘ is a trivalent core atom or molecule having a covalent bond with each of the three dendritic branches, Z is a terminal moiety and "a" and "b" are as defined hereinbefore. An example of such a ternary dendrimer is polyether represented by the following structural formula:

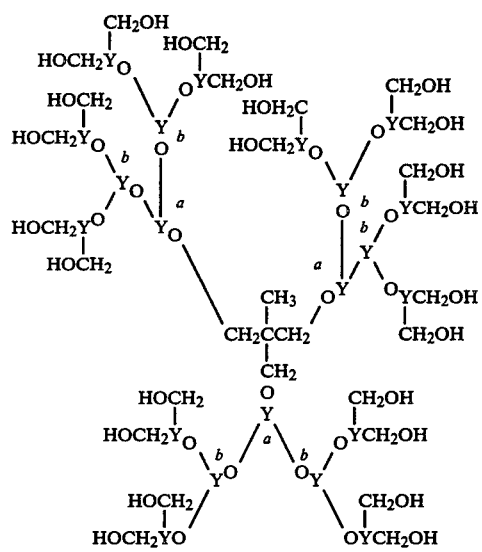

wherein Y represents a trivalent moiety such as —CH(CH$_2$—)$_2$,

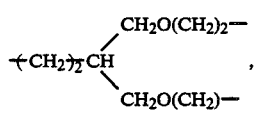

—CH$_2$CHCH$_2$—, or —C(CH$_3$)(CH$_2$—)$_2$ and "a" and "b" indicate first and second generations, respectively. Also, Y may be a tetravalent moiety such as —CH$_2$C(CH$_2$—)$_3$. In these two illustrations, N$_c$ is 3 and N$_r$ is 2. In the latter of the two illustrations, the Repeat Unit is YO. While the foregoing configuration and formula illustrate a trivalent core, the core atom or molecular may be any monovalent or monofunctional moiety or any polyvalent or polyfunctional moiety, preferably a polyvalent or polyfunctional moiety having from 2 to about 2300 valence bonds or functional sites available for bonding with the dendritic branches, most preferably from about 2 to about 200 valence bonds or functional sites. In cases wherein the core is a monovalent or monofunctional moiety, the dense star has only one core branch and must be compared with a linear polymer in order to determine appropriate terminal group density and molecular volume. Accordingly, this dense star must have at least 2 generations in order to exhibit the desired density of terminal groups. Also, Y may be any other trivalent or tetravalent organic moiety such as aryltriyl or aryltetrayl, and the like, with the depicted alkyltriyl moiety being the most preferred. It is further understood that Y may be a polyvalent moiety such as triyls, tetrayls and other poly-yls of aliphatic and aromatic hydrocarbons, e.g.,

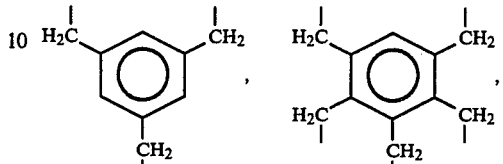

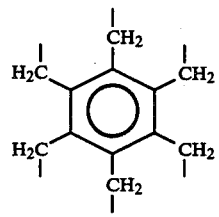

and the like.

In addition to hydroxy, the terminal groups of the dendrimer may be any functionally active moiety that can be used to propagate the dendritic branch to the next generation. Examples of such other moieties include alkoxycarbonyl, amino, alkenyl, aziridinyl, oxazolinyl, haloalkyl, oxiranyl, isothiocyanato and isocyanato, with hydroxy or amino moieties being preferred. While the dendrimers preferably have dendritic branches having 2 to 6 generations, dendrimers having dendritic branches up to 12 generations are suitably made and employed in the practice of this invention.

More preferably, the polyether dendrimers of this invention are represented by the formula:

wherein I is a n-valent core derived from a nucleophilic compound, B is a trivalent moiety capable of linking oxy moieties, n is an integer of 3 or more corresponding to the number of the core branches, Z is oxygen or sulfur and R is hydrogen, alkyl, aryl, alkylaryl, hydroxylalkyl, mercapto alkyl, amine alkyl, acyl and the like wherein each generation is represented by ZB. Also, B may be tetravalent, e.g., —B(ZR)$_3$. More preferably A is a core such as

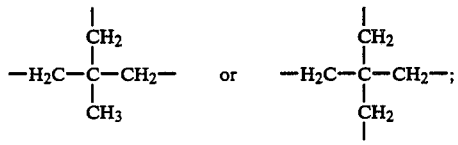

R is hydrogen, methyl, benzyl or aryl; B is alkylene, alkyleneoxyalkylene, polyalkyleneoxyalkylene, arylene, or alkyleneoxyarylene, most preferably an alkylene such as ethylene or propylene; and n is an integer from about 3 to 2000, more preferably from 3 to 1000, most preferably from 3 to 125.

The dense star polymers of this invention are readily prepared by reacting a compound capable of generating a polyvalent core with a compound or compounds which causes propagation of dendritic branches from the core. In one method of preparing these dendrimers (herein called the successive excess reactant method), it is essential to maintain an excess of coreactant to reactive moieties in the terminal groups in the core, core adduct or subsequent adducts and dendrimers in order to prevent cross-linking and to maintain the ordered character of the dendritic branches. In general, this excess of coreactant to reactive moieties in the terminal groups is from about 2:1 to about 1000:1, preferably from about 3:1 to about 120:1 on a molar basis.

Alternatively, the compound capable of generating a polyvalent core, W wherein W is the polyvalent core atom and is covalently bonded to nX reactive terminal groups (n≧2) is reacted with a partially protected multifunctional reagent, T—U) Ⓥ $_m$, wherein U represents a multivalent moiety covalently bonded to m Ⓥ protected moieties (m≧2), and to one T, a moiety capable of reacting with X to form W[(X'—T'—U Ⓥ $_m$]$_n$, wherein X' and T' represent the residue of reaction between X and T. This first generation compound is then subjected to activation conditions whereby the Ⓥ moieties are made reactive (deprotected) and reacted with the partially protected multifunctional reagent, T—U— Ⓥ $_m$, to form the second generation protected dendrimer, W[(X'—T'—U Ⓥ $_m$T'—U Ⓥ $_m$]n. This protected dendrimer can be activated and reacted again in a similar manner to provide the third generation protected dendrimer. Both the successive excess reactant and the partially protected reactant method are specifically illustrated hereinafter.

The successive excess reactant method of preparing the dendrimers is illustrated by the preparation of a ternary dendritic polyamidoamine. In this method, ammonia, a nucleophilic core compound, is first reacted with methyl acrylate under conditions sufficient to cause the Michael addition of one molecule of the ammonia to three molecules of the methyl acrylate to form the following core adduct:

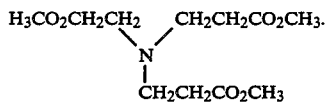

Following removal of unreacted methyl acrylate, this compound is then reacted with excess ethylenediamine under conditions such that one amine group of the ethylenediamine molecule reacts with the methyl carboxylate groups of the core adduct to form a first generation adduct having three amidoamine moieties represented by the formula:

The molar excess of ethylene diamine to methyl acrylate moieties is preferably from 4:1 to 50:1. Following removal of unreacted ethylenediamine, this first generation adduct is then reacted with excess methyl acrylate under Michael's addition conditions to form a second generation adduct having terminal methyl ester moieties:

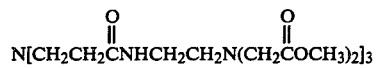

which is then reacted with excess ethylenediamine under amide forming conditions to produce the desired polyamidoamine dendrimer having ordered, second generation dendritic branches with terminal amine moieties. The molar excess of coreactant to reactive moieties in each case is preferably from 1.1:1 to about 400:1, most preferably from about 3:1 to about 100:1. Similar dendrimers containing amidoamine moieties can be made by using organic amines as the core compound, e.g., ethylenediamine which produces a tetra-branched dendrimer or diethylenetriamine which produces a penta-branched dendrimer.

Other dendrimers made by the successive excess reactant method are polysulfides made by (1) reacting a polythiol, C(CH$_2$SH)$_4$, under basic conditions with epichlorosulfide (prepared by method of I. Tabushi et al., *Z. Bull. Chem. Soc. Japan*, 47, 1435 (1974)) to form the first generation polyepisulfide,

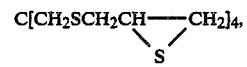

and (2) then reacting this polyepisulfide with hydrogen sulfide to form the first generation polysulfide which can be further reacted with epichlorosulfide and hydrogen sulfide to form subsequent generations. The conditions and procedures which may be suitably employed for polysulfide formation are generally described in Weissberger, *Heterocyclic Compounds with Three- and Four-Membered Rings*, Interscience Publishers, N.Y., 605 (1964) and Meade et al., *J. Chem. Soc.*, 1894 (1948). Polyaminosulfide dendrimers can be prepared by reacting ammonia or an amine having a plurality of primary amine groups with an excess of ethylene sulfide to form a polysulfide and then with excess aziridine to form a fist generation polyaminosulfide which can be reacted with excess ethylene sulfide and then with excess aziridine to form further generations using general reaction conditions described in U.S. Pat. No. 2,105,845 and Nathan et al., *J. Am. Chem. Soc.*, 63, 2361 (1941). The polyether or polysulfide dendrimers can also be prepared by the excess reactant method by reacting hexahalobenzene with phenol of thiophenol to form a first generation polyarylether or polyarylsulfide and then with excess halogen to form the first generation polyhaloarylpolysulfide and then with further phenol or thiophenol to form further generations according to the procedures and conditions as described by D. D. MacNicol et al., *Tetrahedron Letters*, 23, 4131-4 (1982).

The dense star polyethers are preferably prepared by the partially protected reactant method wherein a first organic coreactant,

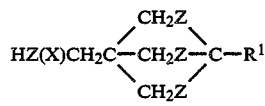

wherein X is a divalent organic radical such as alkylene, arylene, polyalkyleneoxy or polyalkylenethio, Z is oxygen or sulfur, and R$^1$ is hydrogen or alkyl, is first contacted with alkali metal, M°, to form a nucleophilic salt,

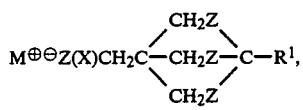

which is then reacted with an electrophilic core, ①(E)$_n$ wherein ① represents a n-valent core such as alkyltriyl [CH$_3$C(CH$_2$—)$_3$], alkyltetrayl [C(CH$_2$—)$_4$] or alkylaryltriyl

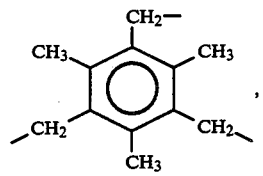

E represents an electrophilic moiety such as tosylate, triflate, halo, sulfate, phosphate, oxiranyl (epoxy), aziridinyl, thioepoxy, oxazolinimum cation or oxazinium cation and n is a number from 1 to 1000, preferably 3 to 100, to a protected first generation adduct,

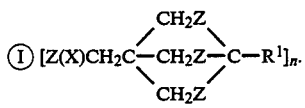

This adduct is then demasked, usually by addition of acid, to form the unprotected first generation adduct,

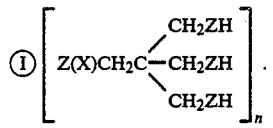

This first generation adduct is contacted with alkali metal to form

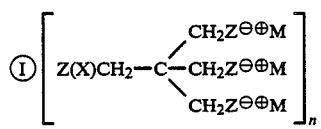

which is then reacted with

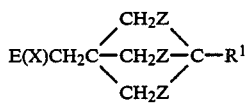

to form the second generation adduct,

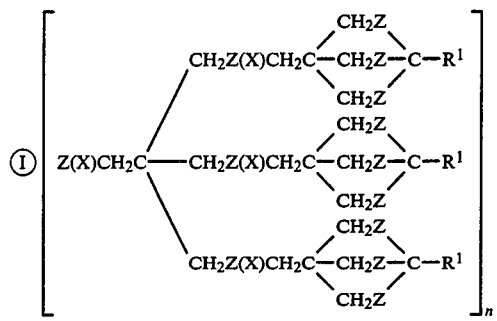

which is then demasked to form the second generation adduct. These generation building steps: metallization, electrophilic reaction and demasking can be repeated to form a third and higher generations until steric hindrance (dense packing) prevents further reaction. It is understood that X groups in one generation are the same, but may differ from X groups in other generations. The same is true for Z groups. Moreover, the foregoing reaction sequence depicts all generation building steps with multiplicity of three,

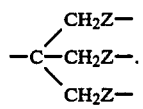

Such multiplicity may be changed from one generation to another. Also, it is understood that the partially protected method may be practiced by reacting a nucleophilic core, ①(Z⊖⊕M)n with an electrophilic first organic coreactant,

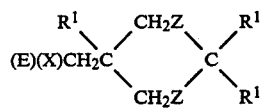

to make the masked first generation adduct.

In an illustrative embodiment of the partially protected reactant method using a nucleophilic core compound, a polyol such as pentaerythritol, C(CH$_2$OH)$_4$, is employed as the polyvalent core generating compound and is converted to alkali metal salt form, e.g., sodium or lithium, by reaction with alkali metal hydroxide or zero valent alkali metal and then reacted with a molar excess of a partially protected compound such as tosylate ester of 1-ethyl-4-hydroxymethyl-2,6,7-trioxabicyclo [2,2,2] octane to form a protected first generation polyether,

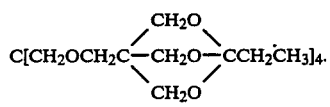

This protected polyether is then activated by reacting with acid such as hydrochloric acid to form the unprotected first generation polyether, C(CH$_2$O—CH$_2$C[CH$_2$OH]$_3$)$_4$. This polether is converted to alkali metal salt form by reaction with alkali metal hydroxide or zero valence alkali metal and then reacted with a molar excess of the partially protected tosylate ether to form the protected second generation polyether. The foregoing sequence is repeated as desired for additional generation development according to conditions and procedures described in Endo et al., *J. Polym. Sci.*, Polym. Lett. Ed., 18, 457 (1980), Yokoyama et al., *Macromolecules*, 15, 11-17 (1982), and Padias et al., *Macromolecules*, 15, 217-223 (1982). These polyether dendrimers are particularly desirable for use in highly alkaline or highly acidic media wherein hydrolysis of a polyamidoamine dendrimer would be unacceptable.

As an example of other dendrimers that are suitable prepared by the partially protected reactants method, polyamine dendrimers may be prepared by reacting ammonia or an amine having a plurality of primary amine groups with N-substituted aziridine such as N-tosyl aziridine,

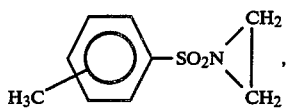

to form a protected first generation polysulfonamide and then activated with acid such as hydrochloric acid to form the first generation polyamine salt and reacted with further N-tosyl aziridine to form the protected second generation polysulfonamide which sequence can be repeated to produce higher generation polyamines using the general reaction conditions described in Humrichause, C. P., PhD, Thesis from University of Pennsylvania, "N-Substituted Aziridines as Alkylating Agents", Ref. No. 66-10, 624 (1966).

In either of the foregoing methods of dendrimer preparation, water or hydrogen sulfide may be employed as nucleophilic cores for the production of binary dendrimers. Examples of other nucleophilic core compounds include phosphine, polyalkylene polyamines such as diethylenetriamine, triethylenetetramine, tetraethylenepentamine and both linear and branched polyethyleneimine; primary amines such as methylamine, hydroxyethylamine, octadecylamine and polymethylenediamines such a hexamethylenediamine; polyaminoalkylarenes such as 1,3,5-tris(aminomethyl)-benzene; tris(aminoalkyl)amines such as tris(aminoethyl)amine; heterocyclic amines such as imidazolines and piperidines; and various other amines such as hydroxyethylaminoethylamine, mercaptoethylamine, morpholine, piperazine, amino derivatives of polyvinylbenzyl chloride and other benzylic polyamines such as tris(1,3,5-aminomethyl)benzene. Other suitable nucleophilic cores include C-30,654D polyols such as the aforementioned pentaerythritol, ethylene glycol and polyalkylene polyols such as polyethylene glycol and polypropylene glycol; 1,2-dimercaptoethane and polyalkylene polymercaptans; thiophenols, and phenols. Of the core compounds, ammonia and the polyalkylene polyamines are preferred for the preparation of polyamidoamine dendrimers by the successive excess reactant method and the polyols are preferred for the preparation of polyether dendrimers by the partially protected reactant method.

Examples of coreactant materials used to react with the nucleophilic core compounds include α,β-ethylenically unsaturated carboxylic esters and amides such as methyl acrylate, ethyl acrylate, acrylonitrile, methyl itaconate, dimethyl fumarates, maleic anhydride, acrylamide, as well as esters, acids and nitriles containing an acrylyl moiety, with methyl acrylate being the preferred coreactant material. In general other preferred unsaturated reactants are volatile or otherwise readily removed from the core/coreactant reaction products without deleteriously affecting the reaction product.

Examples of the second coreactant materials used to react with the adduct of the nucleophilic core and the first coreactant include various polyamines such as alkylene polyamines and polyalkylene polyamines such as ethylenediamine and diethylenetriamine; benzylic polyamines such as tris(1,3,5-aminomethyl)benzene; alkanolamines such as ethanolamine; and aziridine and derivatives thereof such as N-aminoethyl aziridine. Of these second coreactant materials, the volatile polyamines such as ethylenediamine and diethylenetriamine are preferred, with ethylenediamine being especially preferred.

Alternatively, the dendrimers can be prepared by reacting an electrophilic core such as a polyester with a coreactant such as a polyamine to form a core adduct which is then reacted with a suitable second coreactant such as an unsaturated ester to form the first generation polyamidoamine. Thereafter, this first generation product is reacted with a suitable third coreactant such as polyamine and then with the second coreactant such as unsaturated ester to form the desired second generation dendrimer. Examples of suitable electrophilic cores include the $C_1-C_4$ alkyl esters of various polycarboxylic acids such as benzene tricarboxylic acid, oxalic acid, terphthalic acid and various other carboxylic acids represented by the formula:

wherein Y is hydrocarbyl or a hydrocarbon polyl wherein the hydrocarbon radical is alkyl, aryl, cycloalkyl, alkylene, arylene, cycloalkylene, and corresponding trivalent, tetravalent, pentavalent and hexavalent radicals of such hydrocarbons; and P is a whole number from 1 to 6. Other suitable electrophilic core compounds include polyhalohydrocarbons such as polyhaloalkanes, e.g., 1,1,1-tris(chloromethyl)ethane, tetrakis(-bromomethyl)methane, and tris(bromomethyl)hydroxymethyl methane; and polyhaloalkylarenes, e.g., 1,3,5-tris(chloromethyl)-2,4,6-trimethyl benzene, hexakis(-bromomethyl)benzene and 1,2,4,5-tetrakis(bromomethyl)benzene. Preferred electrophilic cores include poly(methyl acrylates), poly(acryloyl chloride), poly(-methacryloyl chloride), alkyl acrylate/alkyl methacrylate copolymers, polymers of alkyl fumarates, and polymers of alkyl itaconates. Of the electrophilic cores, alkyl acrylate/alkyl methacrylate copolymers and alkyl acrylate/alkyl itaconate copolymers are most preferred.

Suitable first coreactant for reaction with the electrophilic core include polyalkylene polyamines such as ethylenediamine, diethylenetriamine, triethylenetetramine and other polyamines represented by the formula:

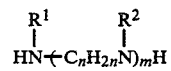

wherein $R^1$ and $R^2$ independently represent hydrogen or an alkyl, preferably $C_1-C_4$ alkyl, hydroxyalkyl, cyanoalkyl, or amido; n is at least 2 and preferably 2 to 6 and m is 2 to 100, preferably 2 to 5. Examples of suitable second coreactants to be used in preparing dendrimers from electrophilic cores include alkyl esters of ethylenically unsaturated carboxylic acids such as methyl acrylate, methyl methacrylate, ethyl acrylate and the like. Examples of suitable third coreactants are those illustrated for the first coreactant.

Thus prepared, the dendrimers can be reacted with a wide variety of compounds to produce the polyfunctional compounds having the unique characteristics that are attributable to the structure of the dendrimer. For example, a dendrimer having terminal amine moieties may be reacted with an unsaturated nitrile to yield a polynitrile (nitrile-terminated) dendrimer. Alternatively, a polyamine dendrimer may be reacted with (1) an α, β-ethylenically unsaturated amide to form a polyamide (amide-terminated) dendrimer, (2) an α, β-ethylenically unsaturated ester to form a polyester (ester-terminated) dendrimer, (3) an oxirane to yield a polyol (hydroxy-terminated) dendrimer, or (4) an ethylenically unsaturated sulfide to yield a polymercapto (thiol-terminated) dendrimer. The polyether dendrimer having terminal hydroxyl moieties may be reacted with carboxylic acids to an ester terminated dendrimer, with alcohol or alkyl halide to form an ether terminated dendrimer, with isocyanate to form a urethane terminated dendrimer, with thionyl chloride to form chloride terminated dendrimer, and with tosylate to form a tosyl terminated dendrimer.

In addition, the dendrimer may be reacted with an appropriate difunctional or trifunctional compound such as an organo polyhalide, e.g., 1,4-dichlorobutane polyesters such as poly(methyl acrylate); polyethers such as polyepichlorohydrin or polyisocyanate or polyisothiocyanate such as toluene diisocyanate, methylene diphenylene diisocyanate and polymers thereof (so-called MDI and polymeric MDI) and other aromatic polyisocyanates, aliphatic polyisocyanates and corresponding polyisothiocyanates, to form a poly(dendrimer) or bridged dendrimer having a plurality of dendrimers linked together through the residues of the polyhalide, polyester, polyether, or polyisocyanate. Dendrimer bridging also results when hydroxyl-terminated dendrimer is mixed with stoichiometric acid amounts of terminated dendrimer under esterification conditions or with hydroxyl-terminated dendrimer is subjected to ether forming conditions.

Such reactions are further exemplified by the following working examples. In such working examples, all parts and percentages are by weight unless otherwise indicated.

EXAMPLE 1

Polyamidoamine Dendrimer-Excess Reactant Method

A. Preparation of Core Adduct

To a one-liter, 3-neck flask equipped with stirrer, condenser and thermowell, and containing methyl acrylate (296.5 g, 3.45 moles) is added at room temperature with stirring over a 6-hour period ammonia (8.7 g, 0.58 mole) dissolved in 102.2 g of methanol. The mixture is allowed to stand at room temperature for 48 hours at which point excess methyl acrylate is removed by vacuum distillation (1 mm Hg at 22° C.) yielding 156 g of residue. This residue is analyzed by size exclusion chromatography ($C_{13}$ NMR) and liquid chromatography. This analysis indicates the coreactant adduct to be the Michael's addition product of 1 mole of ammonia and 3 moles of methyl acrylate at a 97.8 percent yield.

B. Preparation of First Generation Adduct

To ethylenediamine (505.8 g, 8.43 moles) dissolved in 215.4 g of methanol in a 3-liter reaction flask equipped with stirrer, condenser and thermowell, is added the aforementioned ammonia/methyl acrylate adduct (28.1 g, 0.1022 mole), and the reaction mixture is allowed to stand at room temperature for 55 hours. The resulting mixture (747.6 g) is subjected to vacuum distillation to remove excess ethylenediamine and methanol at 2 mm Hg and 72° C. The residue (35.4 g) is analyzed by size chromatography and other suitable analytical techniques. The analyses indicate that essentially all of the ester moieties of the ammonia/methyl acrylate adduct had been converted to amides in the form of a compound represented by the following structural formula:

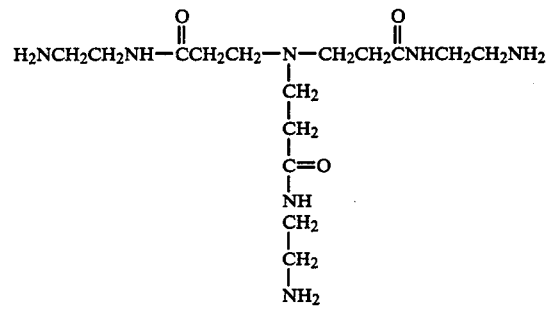

thus indicating a yield of 98.6 percent.

C. Preparation of Second Generation Polyester Dendrimer

To methyl acrylate (93.2 g, 1.084 moles) in a liter flask equipped with condenser, stirrer and thermowell, and heated to 32° C. is added the aforementioned first generation adduct (18 g, 0.0501 mole) dissolved in 58.1 g of methanol over 1.5 hours. The resulting mixture is maintained at 32° C. for an additional 5 hours and allowed to stand an additional 18 hours at room temperature. The reaction mixture (165.7 g) is stripped of methanol and excess methyl acrylate by vacuum distillation (2 mm Hg and 50° C.) to produce 43.1 g of residue. Analysis by suitable techniques indicates the product to be a second generation polyester dendrimer represented by the following formula:

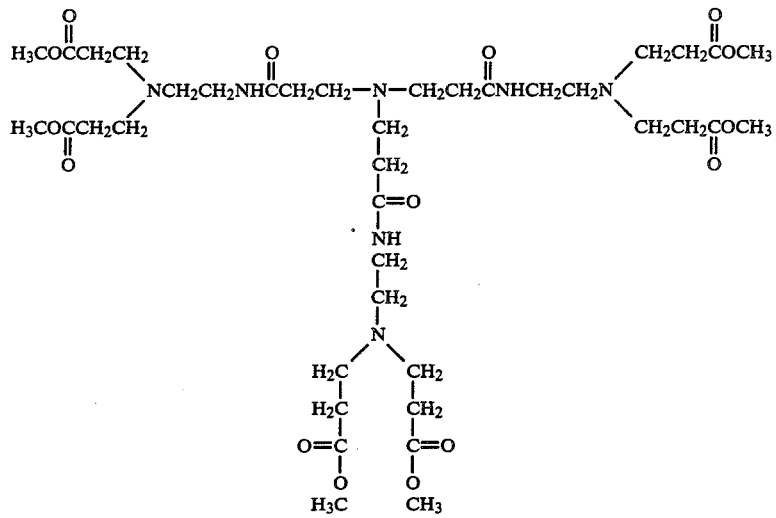

in 98.4 percent yield.

D. Preparation of Second Generation Polyamine Dendrimer

To ethylenediamine (328.8 g, 5.48 moles) dissolved in 210.2 g of methanol at room temperature in the aforementioned flask is added with stirring the second generation polyester dendrimer (34.9 g, 0.0398 mole) dissolved in 45.3 g of methanol. The resulting mixture is allowed to stand for 66 hours at room temperature at which time excess ethylenediamine and methanol is stripped from the product by vacuum distillation (2 mm Hg at 72° C.) to yield 41.1 g (99.0 percent yield) of product. This product is determined by size exclusion chromatography to be the second generation polyamine of the aforementioned polyester dendrimer.

E. Preparation of Third Generation Polyester Dendrimer

To methyl acrylate (65.1 g, 0.757 mole) is added the aforementioned second generation polyamine dendrimer (28.4 g, 0.0272 mole) dissolved in 84.6 g of methanol over a period of 1 hour and 15 minutes. The resulting mixture is allowed to stand for 18 hours at 25° C. after which time excess methyl acrylate and methanol are removed by vacuum distillation (2 mm Hg at 50° C.) to yield 56.3 g (100.0 percent yield) of product residue. Analysis of this residue by suitable analytical techniques indicate that it is a third generation polyester dendrimer having 3 core branches with 4 terminal ester moieties per core branch thereby providing 12 terminal ester moieties per dendrimer molecule.

Preparation of Third Generation Polyamine Dendrimer

To ethylenediamine (437.6 g, 7.29 moles) dissolved in 192 g of methanol is added the aforementioned third generation polyester dendrimer (44.9 g, 0.0216 mole) dissolved in 69.7 g of methanol. The addition occurs over a period of 48 hours at 25° C. with stirring. The resulting reaction mixture is then allowed to stand for 19 hours at 25° C. after which time excess methanol and ethylenediamine are removed by vacuum distillation (2 mm Hg at 72° C.) to yield 51.2 g of residual product. Analysis of this residue indicates a yield of 85.3 percent of a third generation polyamine dendrimer having 3 core branches with 4 terminal primary amine moieties per core branch, thereby providing 12 terminal primary amine moieties per molecule of dendrimer. This dendrimer is calculated to have a molecular volume of 50,000 to 97,000 cubic Å and a density of a terminal amine moiety of 1 to $3(\times 10^{-4})$ moieties/cubic Å.

EXAMPLE 2

Polyuamidoamine Dendrimer Excess Reactant Method

Following the procedure of Example 1, except that a molar equivalent amount of ethylenediamine is substituted for ammonia as the core compound, a third generation polyamine dendrimer is prepared. Upon analysis, it is determined that this dendrimer has four core branches with 4 terminal primary amine moieties per core branch, thereby providing 16 terminal primary amine moieties per molecule of dendrimer. This dendrimer has a molecular volume of 60,000 to 120,000 cubic Å and a terminal amine density of 2 to $6(\times 10^{-4})$ amines/cubic Å.

Similar dendrimers are obtained when equimolar amounts of 1,2-diaminopropane, 1,3-diaminopropane and 1,6-diaminohexane (hexamethylenediamine) are substituted for the ethylenediamine as the core compound in the foregoing procedure. When an equimolar amount of dodecylamine or benzylamine is substituted for the ethylenediamine as the core compound, the resulting dense star polymers have 2 core branches per molecule with 4 terminal primary amine groups per branch, thereby providing a total of 8 primary amine groups per polymer molecule. Substitution of triaminoethylamine for ethylenediamine as the core compound yields a dendrimer having 6 core branches with 4 terminal primary amine moieties per core branch, thereby providing 24 terminal primary amine moieties per molecule of dendrimer.

EXAMPLE 3

Polyamidoamine Dendrimer Excess Reactant Method

A. First Amidation

Following the procedure of Example 1, 5 g (0.0198 mole) of trimethyl-1,3,5-benzenetricarboxylate is mixed with 6.3 g (0.0368 mole) of aminoethylethanolamine ($NH_2CH_2CH_2NHCH_2CH_2OH$) to form a white paste. This mixture is heated at 120° C. for 3 hours to form 9.48 g of a light yellow syrup which infrared and nuclear magnetic resonance spectral analysis indicate is an amidoamine represented by the structural formula:

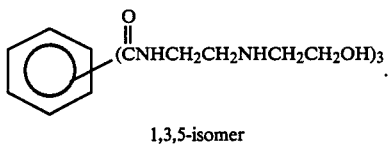

1,3,5-isomer

B. First Alkylation

A 9.48 g (0.0202 mole) of this amidoamine is combined with a stoichiometric excess (11.0 g, 0.127 mole) of methyl acrylate and heated for 24 hours at 80° C. which, after devolatilization, is light yellow syrup weighing 14.66 g. Nuclear magnetic resonance ($H^1$) and infrared spectral analysis of the syrup indicates that it is a triester represented by the structural formula:

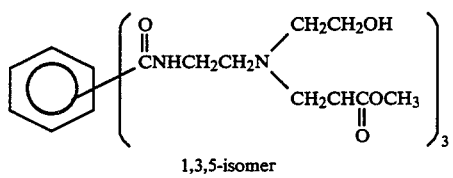

1,3,5-isomer

C. Second Amidation

Following the procedure of part A of this example, the triester (4.57 g, $6.3 \times 10^{-3}$ mole) produced in part B is mixed with 1.96 g ($1.89 \times 10^{-2}$ mole) of aminoethylethanolamine and heated at 90° C. for 48 hours to form 5.8 g of a light yellow, highly viscous syrup. Analysis of this product by nuclear magnetic resonance ($H^1$) (DMSO-$d_6$) and infrared spectroscopy indicates that it is a triamidoamine represented by the structural formula:

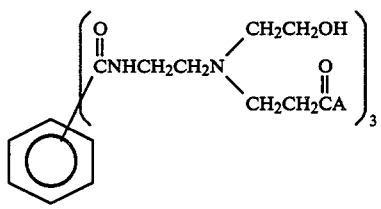

wherein each A is individually

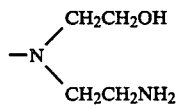

EXAMPLE 4

Polyamidoamine Dendrimer Excess Reactant Method

A. First Amidation

A 27.3-g portion (0.1 mole) of a triester represented by the formula:

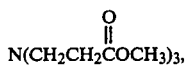

is mixed with 30 g (0.405 mole) of N-methyl ethylenediamine (MEDA) and 16.6 g of methanol and then heated at 63° C. for 11 hours. The product is then stripped of unreacted MEDA and methanol to yield 36.1 g of a triamide represented by the formula:

B. First Alkylation

To the aforementioned triamide (36.1 g, 0.09 mole) is added 38.5 g of methanol to yield a clear solution to which is added 50.5 g (0.59 mole) of methyl acrylate dropwise over a period of 2 hours at 38° C. The temperature of the resulting mixture is increased to 53° C. for 5 additional hours after which unreacted methyl acrylate and methanol are removed under vacuum to yield 61 g of a light yellow syrup. Analysis of this product by nuclear magnetic resonance ($H^1$) spectroscopy indicates that it is represented by the formula:

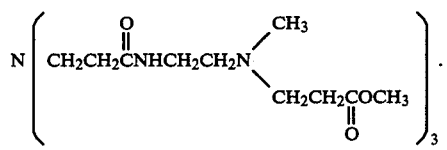

C. Second Amidation

To 60.8 g of the aforementioned first alkylation product are added with stirring 42.7 g of methanol and 26.6 g (0.359 mole) of MEDA followed by heating the resulting mixture at 65° C. for 6 hours. Vacuum stripping of the mixture yields 72.7 g of a light yellow syrup. Analysis of this product (syrup) indicates that it is a mixture of isomers having the following structures:

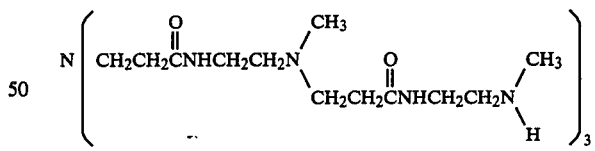

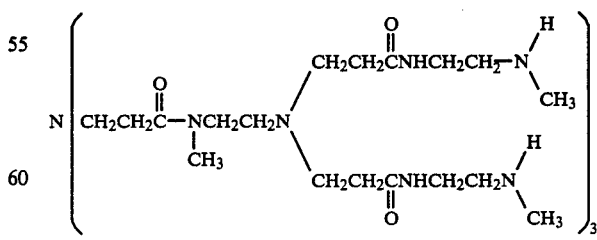

D. Second Alkylation and Third Amidation

Alkylation of the aforementioned second amidation product with methyl acrylate and then amidation of the resulting alkylated product with MEDA in accordance with aforementioned procedures yield a mixture of isomers having core branches with dendritic characteristics.

EXAMPLE 5
Demulsification Method

To 100 ml of an oil-in-water emulsion containing about 5 percent of crude oil having a specific gravity of ~0.98 g/ml is added one part per million based on the emulsion of the dendrimer (ethylene diamine core) of Example 2. The emulsion is then shaken for 3 minutes to effectively disperse the dendrimer into the emulsion. The emulsion is allowed to stand for 10 minutes and visually evaluated. After 10 minutes, the emulsion appears to be completely resolved into two phases having a distinct interface wherein the aqueous phase is essentially transparent.

Following the foregoing procedure except substituting a quaternized form of the foregoing dendrimer for the dendrimer, the emulsion is similarly resolved using 0.5 ppm and 1 ppm of the quaternized form. This quaternized form is prepared by reacting the 32.42 g (0.01 mole) of the dendrimer in 100 ml of methanol with 24.32 g (0.16 mole) of 2-hydroxy-3-chloropropyl trimethyl ammonium chloride in 30 ml of water at 50° C. for about 12 hours.

EXAMPLE 6
Polyalkylenepolyamine Dendrimer Protected Reactant Method

A. Preparation of First Generation Star Polymer

A 35.5 percent solution of $H_2SO_4$ in $H_2O$ is made by dissolving 191.1 g ($H_2SO_4$, 98 percent) in 347 g of deionized water. To this solution, in a 500-ml 3-necked flask equipped with stirrer, condenser and addition funnel, is added neat diethylenetriamine (154.5 g, 1.5 moles), while stirring and cooling (ice) at such a rate that the temperature does not exceed 65° C.–70° C. After this addition, aziridine (21.5 g, 0.5 mole) is added dropwise while stirring and cooling (F.50°) over a period of 0.5 hour. The resulting bright yellow, orange reaction mixture is then stirred while heating at 40° C.–50° C. for 6 hours. To this crude reaction mixture is added 240 g (6.0 moles) of NaOH in portions while stirring. An exotherm is noted which gives a brown-yellow layer which separates from a lower, salt-containing, aqueous layer. The organic (top) layer is separated and found to weigh 287.3 g and contains a substantial amount of water. Solid sodium hydroxide (75 g) is added to this fraction causing a brown layer (top) to separate, which weighs 174.3 g (99 percent of theory). Distillation through a ½×8 inch Vigreux column gives a light yellow liquid, b.p. 123° C.–128° C. at 3 mm Hg, which is determined to be the adduct of 1 mole of aziridine and 1 mole of diethylenetriamine represented by the formula:

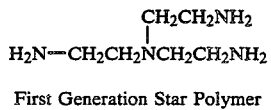

First Generation Star Polymer

B. Preparation of N-(Tosyl)Aziridine p-Toluene sulfonyl chloride (38.0 g, 0.2 mole) is dissolved in 100 ml of diethyl ether in a 250-ml 3-necked flask equipped with stirrer, condenser and addition funnel. To this stirred solution is added triethylamine (20.2 g, 0.2 mole) in a dropwise manner. While stirring and maintaining the reaction temperature at 10° C.–20° C. with an ice-bath, a solution of aziridine (8.6 g, 0.2 mole) in 75 ml of diethyl ether is added dropwise over a period of 15–30 minutes. A thick white precipitate forms. Additional ether (100–150 ml) may be added to facilitate stirring. The reaction mixture is stirred for an additional hour at room temperature and filtered. Washing the filter cake with 2×100 ml portions of ether gives essentially a quantitative yield of $Et_3N$ HCl. Removal of solvent from the filtrate gives light cream colored crystals which weigh 25.0 g (62 percent yield). Recrystallization from $Et_2O$/hexane gives white crystals, m.p. 60° C.–62° C. which are determined by nuclear magnetic resonance to be N-(tosyl)aziridine represented by the formula:

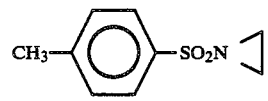

C. Preparation of Protected Polyamine Dendrimer (Second Generation)

The first generation polyamine of Part A (3.5 g, 0.024 mole) and N-tosyl (Tos) aziridine (38.55 g, 0.145 mole) are placed in 50 ml of 95 percent ethanol in a 100-ml vessel equipped with a stirrer. The mixture is stirred at room temperature. Over a period of 2 hours the tosyl aziridine slowly dissolves giving a colorless homogeneous solution after which a white precipitate forms which makes stirring difficult. Additional stirring (1 hour) leads to a solid mass. After adding another 50 ml of ethanol and stirring overnight (25° C.), the white solids are isolated by filtration, washed with 2×100 ml EtOH and 2×150 ml $Et_2O$ and dried by suction. Weight of white solids product is 27.7 g (87 percent). Nuclear magnetic resonance spectral analysis confirms the tosyl hexa-adduct represented by the formula:

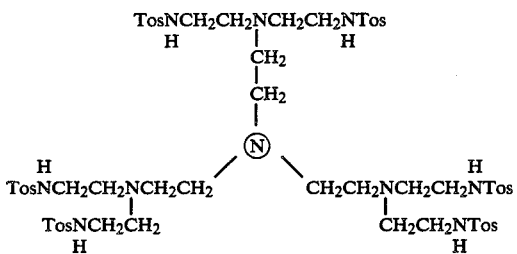

D. Removal of Protecting Tosyl Groups

The protected polyamine dendrimer of Part C (27.7 g, 0.021 mole) is mixed with 130 ml of degassed concentrated sulfuric acid (98 percent) under nitrogen in a one-liter round-bottom flask equipped with stirrer, nitrogen purge and reflux condenser. The mixture is heated at 130° C. for 6 hours. The reaction is complete after 6–10 hours as determined by a test which involves basifying the sample with 10 percent NaOH. The absence of cloudiness at alkaline pH indicates complete reaction. After cooling the reaction mixture to 0° C., diethyl ether (600 ml) is added in small portions to maintain the temperature F.10° C. The resulting white, hygroscopic precipitate is isolated by filtration and then dissolved in water. This water solution is basified to pH>10 with 20 percent KOH. Removal of the water yields a mixture of oily product and solid K₂SO₄. Extraction with methanol (200 ml) and filtration gives the product as a flowable oil, after methanol removal. Upon heating under high vacuum, the remaining volatiles are removed to give a yellow-orange syrup. Nuclear magnetic resonance spectral analysis confirms the aforementioned syrup to be a second generation polyamine dendrimer represented by the formula:

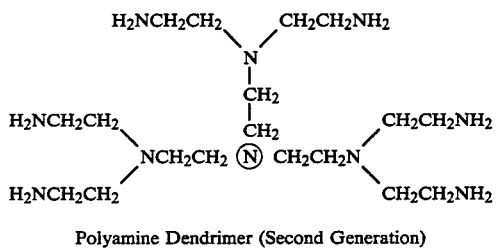

Polyamine Dendrimer (Second Generation)

EXAMPLE 7

A. Transition Metal Ion Control

A 0.1 g portion of the polyamine dendrimer of Part D of Example 6 dissolved in 5 ml of deionized water is added dropwise under ambient conditions to a solution of 0.1 g of copper sulfate in 3 ml of deionized water. A deep blue color accompanied by the formation of a heavy precipitate (floc) is observed. The precipitate is readily removed by centrifugation, then demonstrating the control (removal) of Cu (II) ion by formation of complex between Cu (II) ion and dendrimer.

B. Heavy Metal Ion Control

A 0.1-g portion of the polyamine dendrimer of Part D of Example 6 dissolved in 5 ml of deionized water is added dropwise under ambient conditions to a solution of 0.1 g of uranyl nitrate (UO₂(NO₃)₂6H₂O) dissolved in 3 ml of deionized water. A brilliant yellow color accompanied by the formation of a heavy precipitate (floc) is observed. The resulting complex (precipitate) is isolated by centrifugation, thus demonstrating the ability of dendrimer to control (remove) U (VI) ion formation of complex between the dendrimer and the U (VI) ion.

EXAMPLE 8

Polythioether Protected Reactant Method

A. Preparation of Protected First Generation Star Polymer

A 200-ml, 3-necked flask equipped with stirrer, condenser, nitrogen sparge and addition funnel is charged with 100 ml of ethanol, 7.91 g (0.07 mole) of N-(2-mercaptoethyl)propionamide and 4.76 g (0.07 mole) of sodium ethoxide. The resulting reaction mixture is warmed to 35° C. for one hour while stirring under nitrogen and adding 7.98 g (0.02 mole) of 1,3,5-tris(-chloromethyl)-2,4,6-trimethyl benzene in 25 ml of ethanol over a period of 15 minutes. This reaction mixture is then heated at reflux for 12 hours while stirring. The mixture is then filtered to yield 2.1 g of a white water-soluble salt. The filtrate is evaporated to dryness at 25° C. to yield 14 g of crude product which, after extraction with two 25-ml portions of deionized water, gives 8.2 g (83 percent yield) of a yellow, syrup-like semi-solid. Nuclear magnetic resonance and infrared spectra of the semi-solid indicates a compound represented by the formula:

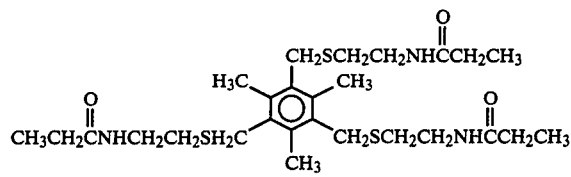

Protected First Generation Star Polythioether

B. Removal of Protecting Moiety

A 5 g (0.01 mole) portion of the protected first generation star polythioether from Part A of this example is dispersed in a mixture of 40 ml of deionized water and 40 ml of 1N HCl, and refluxed for 12 hours at normal pressure. The reaction mixture is neutralized with sodium hydroxide and water is removed to yield a salt which is extracted with toluene in a Soxholet extraction apparatus. After solvent removal, the resulting product is a sticky yellow syrup, weighing 2.27 g (70 percent yield), represented by the following formula:

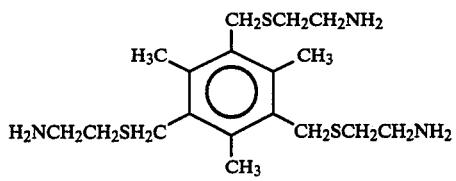

Demasked First Generation Polythioether

EXAMPLE 9

Polythioether Dendrimer Protected Reactant Method

A. Preparation of Protected First Generation Star Polythioether

A 250-ml, 3-necked flask equipped with a stirrer, condenser, nitrogen sparge and addition funnel is charged with 125 ml of absolute ethanol, 13.32 g (0.12 mole) of N-(2-mercaptoethyl)propionamide, 8.16 g (0.12 mole) of sodium ethoxide and 12.7 g (0.02 mole) of hexakis(bromomethyl)benzene. The reaction mixture is stirred under nitrogen while heating at reflux for 12 hours. The orange reaction mixture is filtered to remove 10.95 g of a water-insoluble white solid. The orange filtrate is concentrated by evaporation to one-half of its original volume, thereby depositing 1.99 g of tan crystals (melting point>300° C.). Removal of remaining solvent yields an additional 12.4 g of a tan solid (melting point of 209° C.–260° C.). Nuclear magnetic resonance analysis indicates that the solid is primarily the hexa adduct represented by the formula:

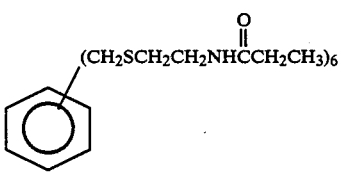

containing some penta adduct

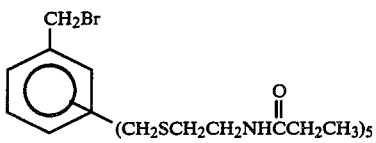

and tetra adduct

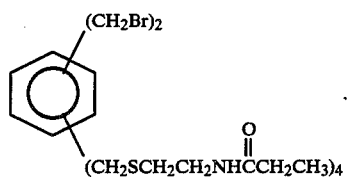

B. Removal of Protecting Moiety

A 5.0-g (0.006 mole) sample of the protected dendrimer of Part A is charged to a 150-ml round-bottom flask equipped with a stirrer and a reflux condenser and containing 40 ml of deionized water and 40 ml of 1N HCl. The mixture is refluxed for 12 hours and neutralized with sodium hydroxide. The resulting mixture is devolatilized to remove water and the solid residue is extracted with toluene. The toluene is removed to provide an amber syrup weighing 2.1 g (75 percent yield based on theoretical hexa adduct). Nuclear magnetic resonance spectral analysis confirms a primary component represented by the formula:

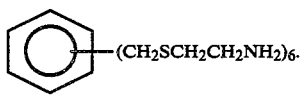

C. Preparation of Copolymeric Dendrimers

Following the procedures for Part E of Example 1, the hexa adduct of Part B of this Example is first contacted with a 12 molar excess of methacrylate to form a copolymeric polyester dendrimer represented by the formula:

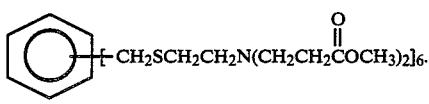

Following the procedure of Part F of Example 1, this polyester dendrimer is contacted with a 240 molar excess of ethylenediamine to form a copolymeric polyamine dendrimer represented by the formula:

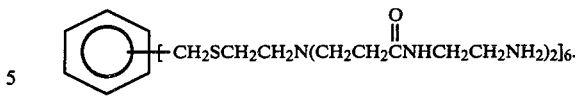

Following the procedure of Parts C and D of Example 6, the hexa adduct of Part B of this Example is first reacted with tosyl aziridine to form a protected copolymeric dendrimer and then demasked with sulfuric acid to form a copolymeric polyamine dendrimer represented by the formula:

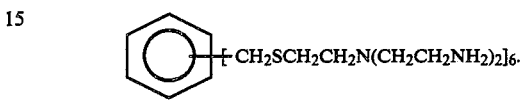

This copolymeric polyamine dendrimer can be reacted first with a 24 molar excess of methyl acrylate to form a copolymeric polyester dendrimer using the procedure of Part E of Example 1 and then with a 960 molar excess of ethylenediamine using the procedure of Part F of Example 1 to form a copolymeric polyamine dendrimer represented by the formula:

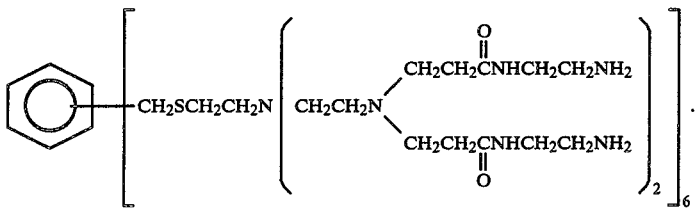

This latter dendrimer is an illustration of a stratified dendrimer in which the repeating or monomeric unit is a thioether (—SCH$_2$CH$_2$N<) in the first generation, an amine (—CH$_2$CH$_2$N<) in the second generation and an amidoamine

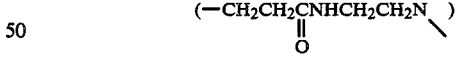

in the third generation and the repeat units are the same within each generation. Thus, each generation constitutes a different strata within the copolymeric dendrimer. Since the stratified dendrimer is also made by combining different monomeric units, it is also copolymeric as opposed to homopolymeric dendrimers which are made from the same monomeric units.

EXAMPLE 10

Polyether Dendrimer Protected Reactant Method

A 125-ml, 3-necked flask equipped with a condenser, stirrer and thermometer is charged with 20 ml of 50 percent NaOH in water, 2.0 g (0.0166 mole) of 1,1,1-tris(hydroxymethyl)ethane, 0.56 g of tetrakis(n-butyl)ammonium hydrogen sulfate, and 40 g (0.156 mole) of a chloroethyl derivative of dioxolane,

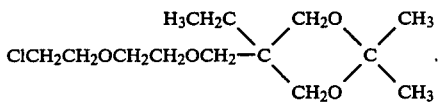

The mixture is warmed at 65° C.±5° C. while stirring for 66 hours after which 10 ml of 50 percent NaOH in water, 0.56 g of (n-butyl)₄NHSO₄ and 10 g of the chloroethyl derivative of dioxolane is added. The heating and stirring is continued for 28 hours at 75° C. The reaction mixture is cooled to room temperature, and extracted with two 50-ml portions of diethylether, dried over anhydrous Na₂SO₄ and concentrated under vacuum at 50° C. to 44.5 g of a yellow oil. After vacuum distillation to remove the unreacted chloroether derivative, the pot residue is analyzed by thin layer chromatography and found to consist of 48.3 percent triadduct represented by the formula:

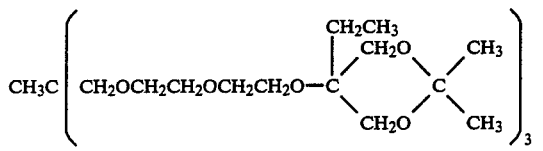

with 44.1 percent of diadduct.

B. Removal of the Protecting Moiety

A 1-g fraction of the triadduct of Part A is charged to a 50-ml round-bottom flask containing 10 ml of 50 percent HCl in H₂O. This mixture is stirred at room temperature for 19 hours, quenched with solid K₂CO₃ and concentrated under vacuum to give an oily, white solid. This solid is stirred in 40 ml of tetrahydrofuran for ½ hour, filtered through a cone of anhydrous Na₂SO₄ to yield 0.86 g of the yellow oil. This product is determined by H'-nuclear magnetic resonance, C¹³ nuclear magnetic resonance and mass spectrometry to be a polyether dendrimer represented by the formula:

The second generation dendrimer is readily prepared by reacting the above first generation dendrimer with additional chloroethyl derivative of dioxolane and then by following the procedures of Parts A and B of this example.

EXAMPLE 11

Polyether Dendrimer Protected Reactant Method

A. Preparation of First Generation Dendrimer

A 250-ml, 3-necked flask equipped with stirrer, condenser and addition funnel is charged with 14.5 g of 4-hydroxymethyl-2,6,7-trioxabicyclo[2.2.2]-octane (HTBO) in 30-ml of diglyme. To this is added 4.5 g of potassium hydride in 120-ml of diglyme at 0° C. over a period of 1.0 hour while stirring the reaction mixture. After 3 hours a 38.3 g portion of pentaerithryl tetrabromide [C(CH₂Br)₄] is added over 0.5 hours while stirring the mixture at 25° C. The mixture is refluxed overnight at 160° C. and poured into water. The resulting white precipitate is filtered, dried and determined to be a compound represented by the formula:

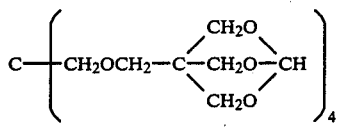

Protected First Generation Dendrimer.

B. Removal of the Protecting Moiety

The dendrimer is then demasked by contacting 2.0 g of the protected dendrimer with 20-ml of deionized water at 90° C. for 2 hours to form the first generation dendrimer represented by the formula:

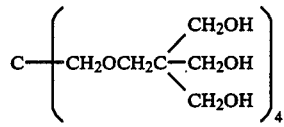

First Generation Polyether.

C. Preparation of Brominated Derivative of First Generation Dendrimer

Into the flask used in Part A is charged 0.1 mole of the first generation dendrimer of Part B in 2.0 mole of pyridine and 1.2 mole of tosyl chloride. The reaction mixture is stirred at room temperature for 5 days and then poured into water to form the dodecyl tosylate of the dendrimer. This tosylate is converted to the dodecyl bromide derivative using the method of Herzog, *Organic Synthesis*, Vol. II, page 476.

D. Preparation of Second Generation Dendrimer

Following the procedure of Parts A and B of this Example, the brominated derivative of Part C is converted to a second generation polyether dendrimer by first reacting it with HTBO to form a protected second generation polyether dendrimer and then demasked with water to form the desired dendrimer represented by the formula:

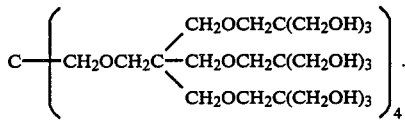

What is claimed is:

1. A dense star polymer having at least one core branch emanating from a core, each core branch having at least one terminal group provided that (1) the ratio of terminal groups to the branches emanating from the core is 2:1 or greater, (2) the density of terminal groups in the dense star polymer is at least 1.5 times that of an extended conventional star polymer having similar core and monomeric moieties and a comparable molecular weight and number of core branches wherein each of such branches of the extended conventional star polymer bears only one terminal group, (3) a molecular volume that is equal to or less than 80 percent of the molecular volume of said extended conventional star polymer, and (4) the two-dimensional molecular diameter of the dense star polymer is in the range from about 12 to about 2000 Angstroms.

2. The dense star polymer of claim 1 having (1) at least 2 core branches per core, (2) a terminal group density at least 5 times that of the corresponding extended conventional star polymer, (3) a molecular volume that is equal to or less than 60 percent of the volume of the extended conventional star polymer, and (4) the two-dimensional molecular diameter of the dense star polymer is in the range from about 25 to about 500 Angstroms.

3. The polymer of claim 1 which is a dendrimer having a polyvalent core that is covalently bonded to at least 1 ordered dendritic branch which extends to two generations such that each dendritic branch has at least four terminal groups and a symmetrical structure.

4. The polymer of claim 1 wherein the core is derived from a nucleophilic compound.

5. The polymer of claim 4 wherein the nucleophilic compound is an amine having a plurality of amine hydrogens.

6. The dense star polymer of claim 1 having at least 3 core branches per core.

7. The dense star polymer of claim 3 having at least 3 core branches per core.

8. A dense star polymer which is a dendrimer represented by the formula:

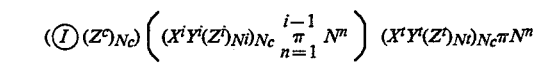

for $i = 0$ to $t = 1$ wherein $\text{\textcircled{I}}$ is a polyfunctional core, $Z_c$ is a functional group bonded to the core and a X group of the first generation, $N_c$ is the number of functional group bonded to the core, $X^i$ is a monofunctional tail of a repeating unit $Y^i$ of the i generation which is bonded to $Y^i$ and a Z group of the $i-1$ generation, $Z^i$ is a functional group bonded to $Y^i$ and a X group of the $i+1$ generation, $N^i$ is a number of at least 2 which corresponds to the multiplicity of the polyfunctional head of $Y^i$, $\pi$ is the product function, $N^{i-1}$ is a number of at least 2 which corresponds to the multiplicity of the polyfunctional head of $Y^{i-1}$ wherein $Y^{i-1}$ is a repeating unit of the $Y^{i-1}$ generation, $X^t$ is the monofunctional tail of a repeating unit $Y^t$ of the terminal generation, $Z^t$ is a terminating group bonded to $Y^t$, $N^t$ is zero or a number which corresponds to the number of $Z^t$ groups bonded to one $Y^t$ group, i represents a number of a particular generation in a series from 1 to a number from 1 to t−1, provided that (1) all $X^iY^i(Z^i)_{Ni}$ are the same within a generation and may be the same or different in different generations and (2) all $X^tY^t(Z^t)_{Nt}$ of the terminal generation are the same.

9. The dense star polymer of claim 8 wherein t is 2 or more and $N^t$ is at least one.

10. The dense star polymer of claim 8 wherein t is 3 or more and $N_t$ is at least two.

11. A functionalized dendrimer which is the reaction product of the dense star polymer of claim 8 and a reagent capable of reacting with the terminal moieties of said polymer.

12. The polymer of claim 1 wherein the dendritic branches contain ether or thioether linkages.

13. The polymer of claim 8 wherein the core is derived from a nucleophilic compound and the branches contain polyether or polythioether moieties wherein the terminal groups are primary amine groups.

14. The polymer of claim 8 wherein the core is derived from a core compound having a plurality of halogens each capable of reacting with an alcohol moiety.

15. The polymer of claim 8 which is represented by the formula:

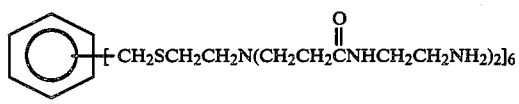

16. The polymer of claim 8 which is represented by the formula:

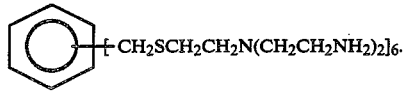

17. The polymer of claim 8 which is represented by the formula:

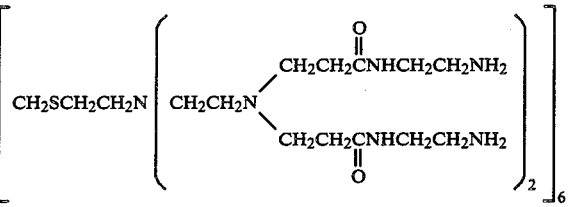

UNITED STATES PATENT AND TRADEMARK OFFICE
CERTIFICATE OF CORRECTION

PATENT NO. : 4,587,329
DATED : May 6, 1986
INVENTOR(S) : Donald A. Tomalia & James R. Dewald It is certified that error appears in the above-identified patent and that said Letters Patent is hereby corrected as shown below:

On the cover page, Sec. 63, "Jan. 1, 1983" should read -- Jan. 7, 1983 --.
On the cover page, Sec. 63, line 3, "which is" should read -- and --.
Column 1, line 11, "Jan. 1, 1983" should read -- Jan. 7, 1983 --.
Column 2, line 15, after "illustrated by" insert -- the --.
Column 3, line 16, "dentritic" should read -- dendritic --.

Column 4, line 25, the word "oompound" should be -- compound --.
Column 4, line 52, after "to form" insert -- a --.
Column 5, line 52, "diameter" should read -- diameters --.
Column 7, line 17, "dentritic" should read -- dendritic --.
Column 7, line 57, after "core functionality" insert -- which is --.

UNITED STATES PATENT AND TRADEMARK OFFICE
CERTIFICATE OF CORRECTION

PATENT NO. : 4,587,329

DATED : May 6, 1986

INVENTOR(S) : Donald A. Tomalia & James R. Dewald

It is certified that error appears in the above-identified patent and that said Letters Patent is hereby corrected as shown below:

Column 9, line 29, that portion of the formula reading

"$O^Y{\diagdown}{\diagup}^Y{\diagdown}OYCH_2OH$ " should read $O^Y{\diagdown}{\diagup}^{OY}{\diagdown}OYCH_2OH$
$\quad\quad\quad\quad\quad |$ $\quad\quad\quad\quad\quad\quad\quad\quad\quad\quad\quad\quad |$
$\quad\quad\quad CH_2OH \quad\quad\quad\quad\quad\quad\quad\quad\quad\quad\quad CH_2OH$ Column 9, line 55, "molecular" should read -- molecule --.

Column 10, line 35, "amino" should read -- amine --.

Column 10, line 45, the word "I" should read --(I)--.

Column 10, line 50, "hydroxylalkyl" should read -- hydroxyalkyl --.

Column 10, line 67, delete "about".

Column 11, line 16, "W", first occurrence, should read -- $W(X)_n$, --.

Column 11, line 29, the formula "$W[(X'-T')U(V)_m T'-U(V)_m]n$" should read -- $W[(X'-T')U(V)_m T'-U(V)_m]n$ --.

Column 12, line 4, that portion of the formula reading $\quad\quad\quad\quad O \quad\quad\quad\quad\quad\quad\quad\quad\quad\quad\quad O$
$\quad\quad\quad\quad \| \quad\quad\quad\quad\quad\quad\quad\quad\quad\quad\quad \|$
" $(CH_2COCH_3)$" should read -- $(CH_2CH_2COCH_3)$ --.

UNITED STATES PATENT AND TRADEMARK OFFICE
CERTIFICATE OF CORRECTION

PATENT NO. : 4,587,329

DATED : May 6, 1986

INVENTOR(S) : Donald A. Tomalia & James R. Dewald

It is certified that error appears in the above-identified patent and that said Letters Patent is hereby corrected as shown below:

Column 12, line 41, the word "fist" should read -- first --.

Column 12, line 49, the word "of" should read -- or --.

Column 13, line 30, after "to" insert -- form --.

Column 14, line 65, "polether" should read -- polyether --.

Column 15, line 11, "suitable" should read -- suitably --.

Column 15, line 12, "reactants" should read -- reactant --.

Column 15, line 42, "a" should read -- as --.

Column 15, line 51, delete "C-30,654D".

Column 16, line 56, "coreactant" should read -- coreactants --.

Column 18, line 27, before "chromatography" add -- exclusion --.

Column 18, line 53, before "liter" add -- one --.

Column 19, line 55, the title "Preparation of Third Generation Polyamine Dendrimer" should read -- F. Preparation of Third Generation Polyamine Dendrimer --.

Column 20, line 30, "Polyuamidoamine" should read -- Polyamidoamine --.

Column 21, line 17, before "light" add -- a --.

UNITED STATES PATENT AND TRADEMARK OFFICE
CERTIFICATE OF CORRECTION

PATENT NO. : 4,587,329
DATED : May 6, 1986
INVENTOR(S) : Donald A. Tomalia & James R. Dewald It is certified that error appears in the above-identified patent and that said Letters Patent is hereby corrected as shown below:

Column 21, lines 56-59, $$`` -N\begin{smallmatrix}CH_2CH_2NH_2\\CH_2CH_2OH\end{smallmatrix} \text{''  should read}$$

$$-- -N\begin{smallmatrix}CH_2CH_2OH\\CH_2CH_2NH_2\end{smallmatrix} \quad \text{or} \quad -NHCH_2CH_2NHCH_2CH_2OH --.$$

Column 25, line 2, the formula "pH>10" should read --pH≥10--.

Signed and Sealed this

Twenty-first Day of June, 1994

Attest:

BRUCE LEHMAN

Attesting Officer    Commissioner of Patents and Trademarks